United States Patent
Chang et al.

(10) Patent No.: US 6,459,085 B1
(45) Date of Patent: Oct. 1, 2002

(54) DEPTH OF INTERACTION SYSTEM IN NUCLEAR IMAGING

(75) Inventors: Wei Chang, Lisle; Kenneth Matthews, Chicago; Caesar Ordonez, Aurora, all of IL (US)

(73) Assignee: Rush Presbyterian-St. Luke's Medical Center, Chicago, IL (US)

( * ) Notice: Subject to any disclaimer, the term of this patent is extended or adjusted under 35 U.S.C. 154(b) by 0 days.

(21) Appl. No.: 09/427,362

(22) Filed: Oct. 26, 1999

(51) Int. Cl.$^7$ .................................................. G01J 27/00
(52) U.S. Cl. ......................... 250/370.11; 250/370.01; 250/370.09; 250/591; 250/367
(58) Field of Search .................... 250/370.11, 390.11, 250/580, 586, 363.03, 370.01, 369.03, 370.09, 591, 367

(56) References Cited

U.S. PATENT DOCUMENTS

| | | | |
|---|---|---|---|
| 5,103,098 A | 4/1992 | Fenyves | 250/368 |
| 5,122,667 A | 6/1992 | Thompson | 250/363 |
| 5,349,191 A | 9/1994 | Rogers | 250/367 |
| 5,376,795 A | 12/1994 | Hasegawa et al. | 250/363.04 |
| 5,410,153 A | 4/1995 | Ferreira | 250/363.09 |
| 5,444,253 A | 8/1995 | Berlad | 250/369 |
| 5,561,297 A | 10/1996 | Engdahl | 250/369 |
| 5,576,547 A | 11/1996 | Ferreira et al. | 250/369 |
| 5,600,144 A * | 2/1997 | Worstell | 250/363.03 |
| 5,698,850 A | 12/1997 | Nagai | 250/252.1 |
| 5,760,401 A | 6/1998 | Nellemann et al. | 250/363.03 |
| 5,783,829 A | 7/1998 | Sealock et al. | 250/367 |
| 5,841,140 A | 11/1998 | McCroskey et al. | 250/363.03 |
| 5,900,636 A | 5/1999 | Nellemann et al. | 250/363.04 |
| 6,078,052 A | 6/2000 | DiFilippo | 250/367 |
| 6,100,532 A | 8/2000 | Bryman | 250/369 |
| 6,124,595 A | 9/2000 | Engdahl et al. | 250/366 |
| 6,194,728 B1 | 2/2001 | Bosnjakovic | 250/372 |
| 6,271,510 B1 | 8/2001 | Boxen | 250/370.11 |
| 6,288,399 B1 | 9/2001 | Andreaco et al. | 250/368 |

OTHER PUBLICATIONS

P. Bartzakos. and C.J. Thompson, "A Depth–Encoded PET Detector," *IEEE Transactions on Nuclear Science* 38(2), pp. 732–738, Apr. 1991.

A. Weisenerger et al., "Low cross–talk fiber readout of scintillation detectors," *IEEE Trans. Nucl. Sci.* NS–40, pp. 455–460, 1993.

(List continued on next page.)

*Primary Examiner*—Georgia Epps
*Assistant Examiner*—M. Hansan
(74) *Attorney, Agent, or Firm*—Foley & Lardner

(57) ABSTRACT

A device and method for determining the x- and y-positions, as well as the depth of interaction, of an interaction between a gamma ray and a scintillation crystal. In one embodiment, a first and a second sensor array are disposed on opposite sides of a scintillation crystal which is subjected in incident gamma radiation resulting in the release of photons. The first sensor array provides a measurement of the x- and y-positions of the interaction while the second sensor array provides a measurement of the depth-of-interaction. In one embodiment, the first sensor array is a photomultiplier array and the second sensor array is an array of wavelength-shifting fibers.

25 Claims, 14 Drawing Sheets

OTHER PUBLICATIONS

R. Wojcik et al., "Embedded waveshifting fiber readout of long scintillators," *IEEE Trans. Nucl. Sci. NS–40*, pp. 470–475, 1993.

D. Gagnon et al., "Maximum Likelihood Positioning in the Scintillation Camera Using Depth of Interaction," *IEEE Transaction on Medical Imaging 12*(1), pp. 101–107, Mar. 1993.

W. W. Moses and S. E. Derenzo, "Design Studies for a PET Detector Module Using a Pin Photodiode to Measure Depth of Interaction," *IEEE Transactions on Nucl. Sci. 41*(4), pp. 1441–1445, Aug. 1994.

M. B. Williams et al., "PET detector using waveshifting optical fibers and microchanel plate PMT with delay line readout,"*IEEE Trans. Nucl. Sci. NS–45*, pp. 195–205, 1998.

W. Worstell et al., "First results with high resolution PET detector modules using wavelength–shifting fibers," *Conference Record of the 1997 IEEE NSS/MIC*(2), pp. 934–938, 1998.

R.S. Miyaoka et al., "Design of a Depth of Interaction (DOI) PET Detector Module," *IEEE Transactions on Nuclear Science 45*(3), pp. 1069–1073, Jun. 1998.

A. J. Soares et al., "Development of a small gamma camera using wavelength–shifting fibres coupled to inorganic scintillation arrays for imaging 10 kev gamma rays," *Conference Record of the 1998 IEEE Nuclear Science Symposium and Medical Imaging Conference*(2), pp. 1277–1284, 1999.

Y. Shao and Simon R. Cherry, "A Study of Depth Interaction Using Bent Optical Fibers," *IEEE Transactions on Nuclear Science 46*(3), pp. 618–623, Jun. 1999.

\* cited by examiner

Illustration of a gamma camera detector with an integrated WLS fiber array for depth-of-interaction measurement (exploded view)

Emission and absorption spectra of a Bicron's BCF-91A WLS fiber (Bicron, 1999)

Illustration of a 10-PMT-sharing scheme for readout of 17 bundles of WLS fibers.

DEPTH OF INTERACTION SYSTEM IN NUCLEAR IMAGING

The present invention is directed to a method and system for determining depth of interaction (DOI) of gamma rays with a scintillation crystal used in a nuclear imaging apparatus. More particularly the invention is directed to a method and system for establishing the depth of interaction of gamma rays by use of scintillating wavelength-shifting fibers disposed near the scintillation crystal. These fibers assess the distribution width of scintillation light received from the scintillation crystal to establish depth of interaction.

A variety of nuclear imaging methodologies are in wide spread use in the medical community. These systems include, for example, Anger (gamma) cameras and positron emission tomography (PET). In the case of the Anger gamma camera shown in an exploded view in FIG. 1, these systems have been an important part of nuclear medicine laboratories for many years. The Anger camera also determines the distribution of radio pharmaceuticals in a patient. Projection images are derived over a short time period by determining sequentially the coordinates (x,y) of the gamma ray interaction site of each legitimate photon in the scintillator crystal. The nuclear images which are produced have diminished resolution as a result of the uncertainty in depth of gamma ray interaction with the scintillator crystal.

PET has found significant clinical applications because of the favorable biodistribution of positron tracers, such as F-18 FDG. Because of the high costs associated with dedicated PET scanners, dual-head Anger (gamma) camera systems, normally used for single-photon emission computed tomography (SPECT) and whole body imaging, have attracted commercial interest as an alternative to PET systems for the imaging of positron tracers. The two opposed Anger cameras detect in coincidence the pair of 511 keV photons emitted from the annihilation of a positron and a local electron. Ideally, the annihilation site is localized to lie along a line connecting the detected interaction positions in the two opposed cameras. After collecting a large number of such coincidence events, image reconstruction techniques are used to derive the three-dimensional distribution of the positron tracer. Most PET systems use ring- or cylinder-shaped detectors to achieve $2\pi$ coverage and data sampling. With dual-head Anger cameras, although rotation of the cameras can achieve the same sampling, the detector coverage is only about ⅓ of the $2\pi$ circumferential coverage of dedicated PET systems.

Because dedicated PET systems are optimized for coincidence imaging, the quality of PET images will always be superior to that of images obtained with multi-purpose dual-head Anger cameras. Lower photon detection efficiency and modest reconstructed spatial resolution are the primary reasons why the image quality for coincidence imaging with dual-head Anger cameras lags behind that of dedicated PET systems. The detection efficiency for 511 keV gamma rays in a 9.5 mm (⅜") thick NaI(Tl) crystal used in standard Anger cameras is slightly less than one-third that of a conventional 25 mm (1.0") thick BGO crystal. Therefore, the intrinsic detection efficiency for coincidence measurements (proportional to the square of the detection efficiency of a single detector) with dual-head Anger cameras is only about one-tenth that of a BGO-based PET system of the same solid angle coverage. However, if the loss of image quality is within acceptable limits to provide diagnostic information, the much lower cost of a dual-head Anger camera system compared to a dedicated PET system is very attractive and should justify further investigation and optimization of coincidence imaging techniques with dual-head Anger cameras. Coincidence imaging with dual-head Anger cameras can be a practical way for many community hospitals to offer positron imaging capabilities to their patient population. All the major camera manufacturers now offer dual-head Anger camera systems with coincidence imaging capability, such as ADAC's MCD, Picker's γPET, GE's CoDe5 and Siemen's e-cam.

To boost detection efficiency and stopping power, camera manufacturers have since increased the thickness of the scintillation crystals of their dual-head systems from the previous ⅜" to ⅝". One manufacturer even goes up to ¾" in crystal thickness. A direct consequence of using thick crystals is degraded intrinsic spatial resolution. The increased thickness causes greater spreading of scintillation light from interaction sites in the crystal. The effect of light spreading is less of a problem for coincidence imaging than for low-energy single-photon imaging because 511 KeV photons penetrate more deeply into the crystal—less spreading of light occurs for interactions deep in the scintillation crystal. The loss of intrinsic resolution for single-photon imaging is marginally acceptable, mainly because collimator resolution is more important than intrinsic resolution in single photon imaging. Therefore, the use of thicker crystals in Anger cameras is a practical, but not optimal, compromise for an imaging system designed for both single-photon and positron-coincidence imaging.

Another consequence of using thick crystals is parallax error, which manifests as degraded reconstructed image resolution in coincidence imaging. Parallax error occurs when gamma rays enter the detector obliquely. The true interaction position for gamma ray γ is at depth z and transverse position x. In a detector that does not provide DOI information (e.g., a conventional Anger camera), all gamma rays that interact at the transverse position x are assumed to have the same depth coordinate z' (the average depth of interaction). This assumption often misplaces the detection site of the gamma ray. For single-photon imaging, this mispositioning is not significant because gamma rays are constrained by most collimators to enter the crystal at normal or near-normal angles of incidence. For coincidence imaging, which does not use collimators, 511 keV photons can enter the detectors obliquely; mispositioning can occur for both detected annihilation photons in a coincidence event. PET reconstruction algorithms assume that the source activity is located along the line joining the sites of the two detected photons. Consequently, if the endpoints of the line are mispositioned, the reconstructed source distribution is inaccurate. The error in the reconstruction caused by this mispositioning is reflected by degraded spatial resolution. For example, for a cylindrical system, the spatial resolution is degraded in the radial resolution in the peripheral imaging field; and for planar detector-based systems (such as dual head Anger cameras) blurring due to parallax is more an elliptical blur at r=o, as opposed to r>o for cylindrical systems. Note that this parallax error is more significant when thick crystals are used, and when large-area plate detectors are used for coincidence imaging of positron sources distributed over large volumes, the situation encountered in using dual-head cameras for coincidence imaging of the body.

Therefore, the best detection sensitivity and reconstructed image resolution in coincidence imaging with dual-head Anger cameras can be achieved by using thick scintillation crystals and making real-time DOI measurements along with the conventional x and y positions.

Various techniques to obtain DOI information in scintillation detectors have been proposed in the last dozen years. Most of these techniques were for PET, and to date there has been no practical technique that is applicable to commercial Anger cameras.

In one method in 1986, two different layers of scintillation detectors were used which were optically coupled to each other. The interactions that occur in each layer are distinguished based on the different decay times of the two scintillators. A phoswich detector can be used and this consists of a layer of LSO optically coupled to a layer of YSO or NaI(Tl). The phoswich detector is intended for both single-photon and coincidence imaging; it provides DOI information in terms of the layer in which the interaction occurs based on scintillation decay time. In another effort, DOI information was asserted to be inherent in the Anger camera system and should be derivable from the signals of the PMT array. However, experimental confirmation of their simulation studies have not been reported yet.

In yet another work, it was proposed to use the temperature-dependent behavior of scintillation decay time for measuring DOI. It has been demonstrated that applying a temperature gradient to NaI(Tl) or BGO crystals can yield DOI information based on temperature-induced variations in scintillation decay time for events detected at different depths in the crystal. A position-sensitive-PMT has been coupled to the side of a piece of flat BGO crystal plate for DOI determination in an animal PET imager. Although the DOI can be determined with excellent accuracy, their detector provides only one or two thin imaging slices in the axial direction. While satisfactory for an animal imager, this is not a practical design for imaging human patients.

OBJECTS OF THE INVENTION

It is therefore an object of the invention to provide an improved nuclear imaging method and system.

It is another object of the invention to provide an improved nuclear imaging system for determining depth of interaction of a gamma ray interacting with a scintillation crystal.

It is also an object of the invention to provide an improved PET system and method of use for establishing DOI information for improvement of PET images.

It is a further object of the invention to provide an improved Anger camera system and method of use for establishing DOI information for improvement of nuclear imaging.

It is in addition an object of the invention to provide an improved gamma ray coincidence imaging technology for depth of interaction analysis in an Anger gamma camera, a positron emission tomography system and any system in which gamma radiation undergoes a depth of interaction photoscintillation event.

It is still another object of the invention to provide an improved apparatus and method for establishing DOI information for nuclear imaging using scintillating wavelength-shifting fibers.

It is yet another object of the invention to provide an improved computer means and executable computer software for evaluating nuclear data and determining DOI information for use in improving nuclear imaging.

It is still an additional object of the invention to provide an improved method and system for evaluating nuclear data for determining qualitative accuracy in a nuclear image.

It is yet a further object of the invention to provide an improved method and system for determining depth of interaction corrections for PET systems with large area detector plates including PENN-PET and cylindrical nanocrystal based-PET.

Other objectives and advantages of the invention will be apparent from the detailed description and drawings described hereinafter.

DETAILED DESCRIPTION OF PREFERRED EMBODIMENTS

Figure 3:
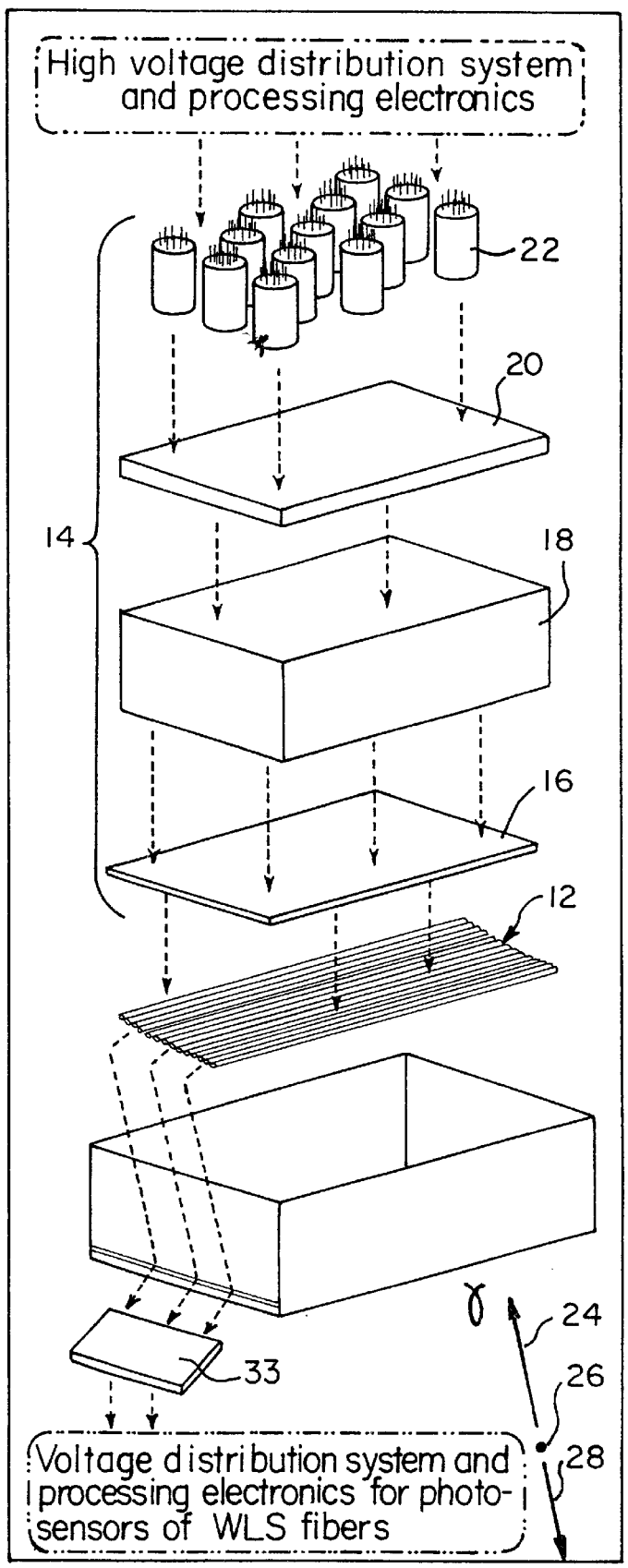
FIG. 3 illustrates an exploded view of imaging components of one form of the invention.

A nuclear imaging system 10 constructed in accordance with one form of the invention is shown in FIG. 3. In the exploded view of FIG. 3 for the components of the nuclear imaging system 10, wavelength-shifting scintillating (WLS) fibers 12 are disposed on the entrance side of a stack of elements 14 of the imaging system 10. The stack of elements 14 include a glass entrance window 16 which is optically bonded to a scintillation crystal 18, such as NaI(Tl), lutetium orthdsilicate (LSO) or bismuth germanate. On the exit side of the crystal 18 is a glass exit window 20 optically bonded to the crystal 18 on one side and on the other side to a light sensor array 22, such as a photomultiplier array. During operation of the system 10, a gamma ray 24 from a positron source 26 is emitted (along with a companion gamma ray 28 in the opposite direction). The array 22 senses the photons created by a gamma ray 24 interacting with the crystal 18. This sensor array 22 is the conventional part of the system 10.

In the nuclear imaging system shown in FIG. 3: the processing electronics connect to the PMT array and an external acquisition computer; the PMT array is optically bonded to the glass exit window and typically will have 70–20 PMTs; a glass exit window is optically bonded to the PMT array and the NaI(Tl) crystal; the front and back faces of the NaI(Tl) scintillation crystal are optically bonded to the extrance and exit glass windows; a glass entrance window is optically bonded to the NaI(Tl) crystal and the WLS fiber ribbon; the back face of the ribbon array of wavelength-shifting scintillating (WLS) fibers is optically bonded to the glass entrance window, while the front face is covered with reflective powder; a5-sided protective aluminum scintillator housing surrounds the NaI(Tl) crystal, glass windows, and fiber ribbon; the housing is hermetically sealed to the edges of the glass entrance and exit windows, and provides an egress for the fiber ribbon at one edge; photosensors (e.g. photodiodes or PMTs) are optically coupled to one end of each WLS fiber; the photosensors have dedicated processing electronics that connect to the external acquisition computer; and the entire assembly is housed within a radiation-shielded camera enclosure. Note: vertical dimensions are exaggerated and not to scale.

For purposes of illustrating operation of the system 10, we will describe events only for the gamma ray 24 although the description will also characterize events for the gamma ray 28 as well in a dual-head gamma camera or positron emission tomography system, wherein a pair of 511 keV photons are created by annihilation of a positron with a local electron. The gamma ray 24 therefore enters the scintillation crystal 18; and as shown in the isolated partial section view of FIG. 4, the gamma ray 24 enters obliquely and undergoes a scintillation interaction event at location "z" along line "x". Consequently, since it is assumed that the gamma ray 24 undergoes an interaction, or scintillation, event at z' (at an average thickness of the crystal 18), parallax error is introduced into forming a nuclear image characteristic of the patient being imaged (see for example FIG. 2). Therefore, the sensor array 22 establishes an accurate positron in x,y coordinates, but an inaccurate depth of interaction z position. For single-photon imaging, this mispositioning is not significant because generally gamma rays are constrained by the collimator to enter the crystal at normal or near-normal angles of incidence. For coincidence imaging, which does not use collimators, 511 keV photons can enter the detectors obliquely; mispositioning can occur for both detected annihilation photons in a coincidence event. PET reconstruction algorithms assume that the source activity is located along the line joining the sites of the two detected photons. Consequently, if the endpoints of the line are mispositioned, the reconstructed source distribution is inaccurate. The error in the reconstruction caused by this mispositioning is reflected by degraded spatial resolution, most notably the radial resolution in the peripheral imaging field. Note that this parallax error is more significant when a thick scintillation crystal 18 is used, and when large-area plate sensor arrays 22 are used for coincidence imaging of positron sources distributed over large volumes—the situation encountered in using dual-head cameras for coincidence imaging of the body.

Figure 6:
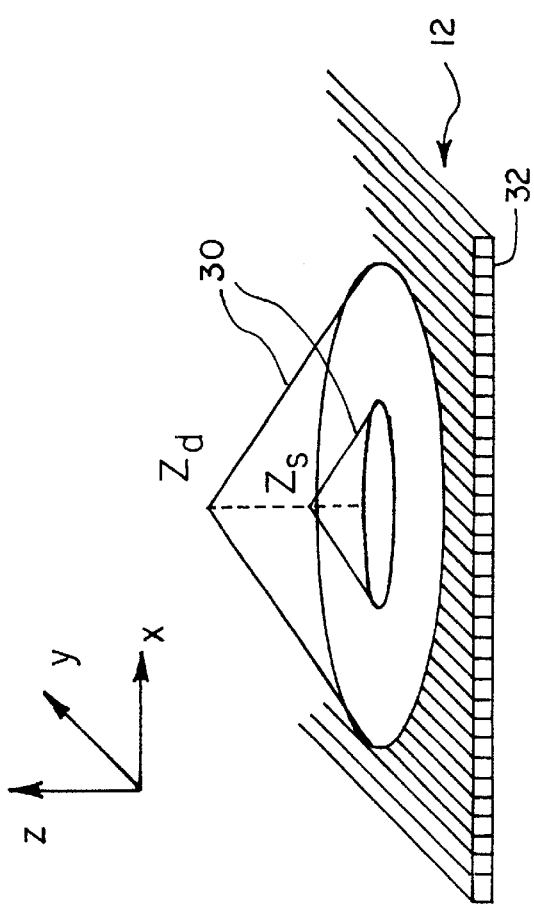
FIG. 6 illustrates several example exiting conical light distributions from a scintillation crystal for two depths of interaction.
Figure 8:
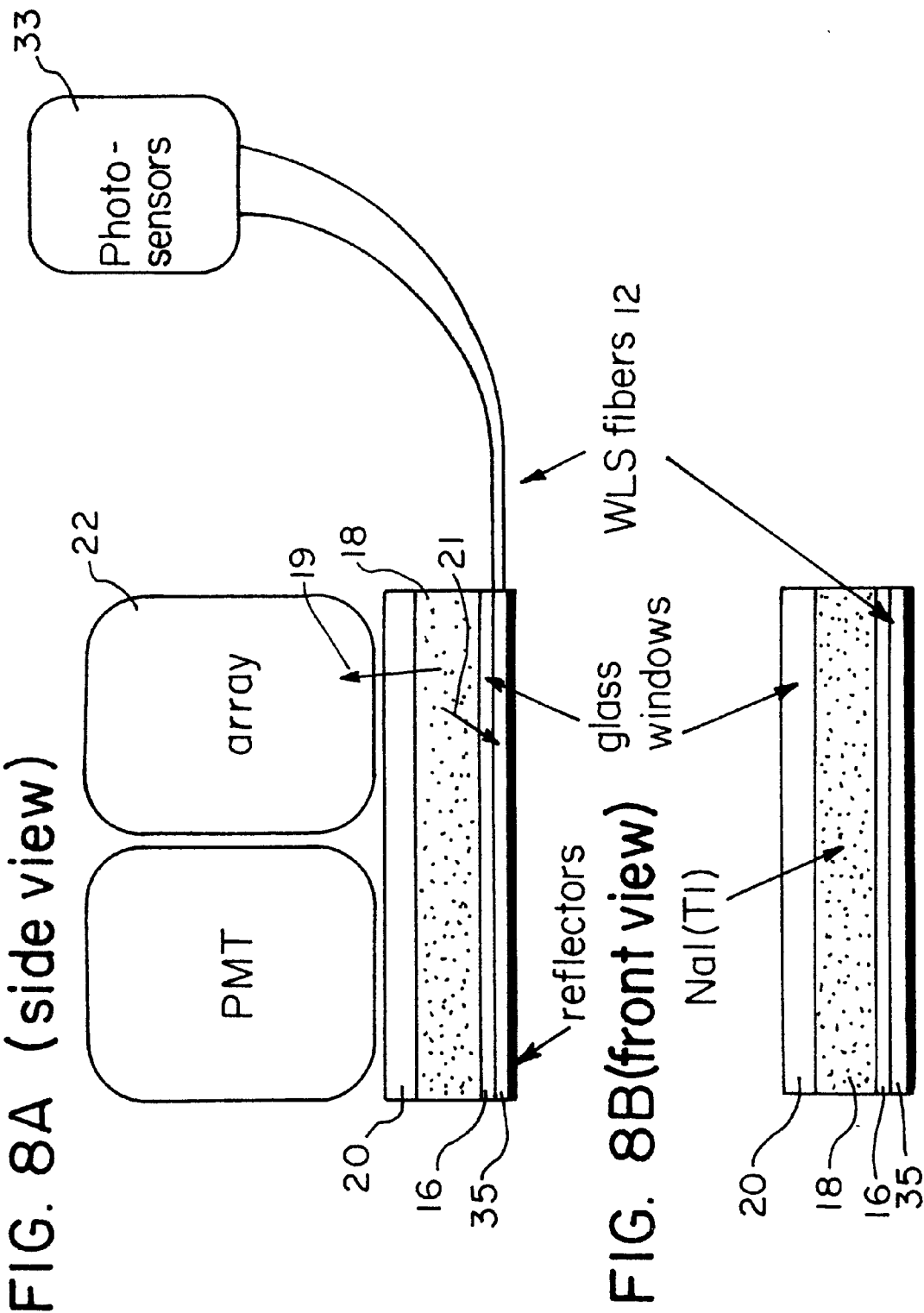
FIG. 8A is a side view of the nuclear imaging detector components of the invention.
FIG. 8B is a front view thereof.

Referring to FIGS. 8A and 8B, after the incident gamma ray 24 imparts its energy in the scintillation crystal 18, a large number of blue scintillation photons 19 are emitted isotropically from the point of interaction z. The number of the emitted photons is proportional to the energy deposited by the gamma ray 24. Some of the emitted photons 19 are transmitted through the exit window 20 and are detected by the sensor array 22. For scintillation photons 21 emitted towards a relatively smooth optical interface between the scintillation crystal 18 and the glass entrance window 16, there is a finite probability that the photons 21 will pass through the window 16 and reach the WLS fibers 12. When the photons 19 strike the WLS fibers 12, further photo scintillation events occur. The collected light is transmitted along each of the fibers 32 and collected by a photosensor 33. The WLS fibers 12 absorb the scintillation photons from the crystal 18 after the gamma ray interaction. The absorbed energy is reemitted as secondary photons of longer wavelengths: the reemission wavelength is characteristic of the scintillator dopant in the WLS fibers 12. A small fraction of these secondary photons will propagate to the ends of the fibers 32 to be measured by the photosensor 33. Absorption and emission spectra of the Bicron BCF-91A blue-to-green form of the WLS fibers 12 are shown in FIG. 6. The absorption spectrum is well matched to the emission spectra of NaI(Tl) and CsI(Na). The fiber's emission spectrum peaks in the green wavelengths.

The probability of the photons 21 reaching the fibers 12, called the Fresnel transmission coefficient, depends on the angle of incidence and becomes zero when the angle of incidence exceeds a critical angle. Because of azimuthal symmetry, this critical angle defines a cone 30 (see FIG. 6). Scintillation photons emitted within this cone 30 are the predominant component of the photoscintillation signals generated in the WLS fibers 12. For an interface between the NaI(Tl) form of the scintillation crystal 18 and the glass entrance window 16, the critical angle is about 54°.

Figure 5:
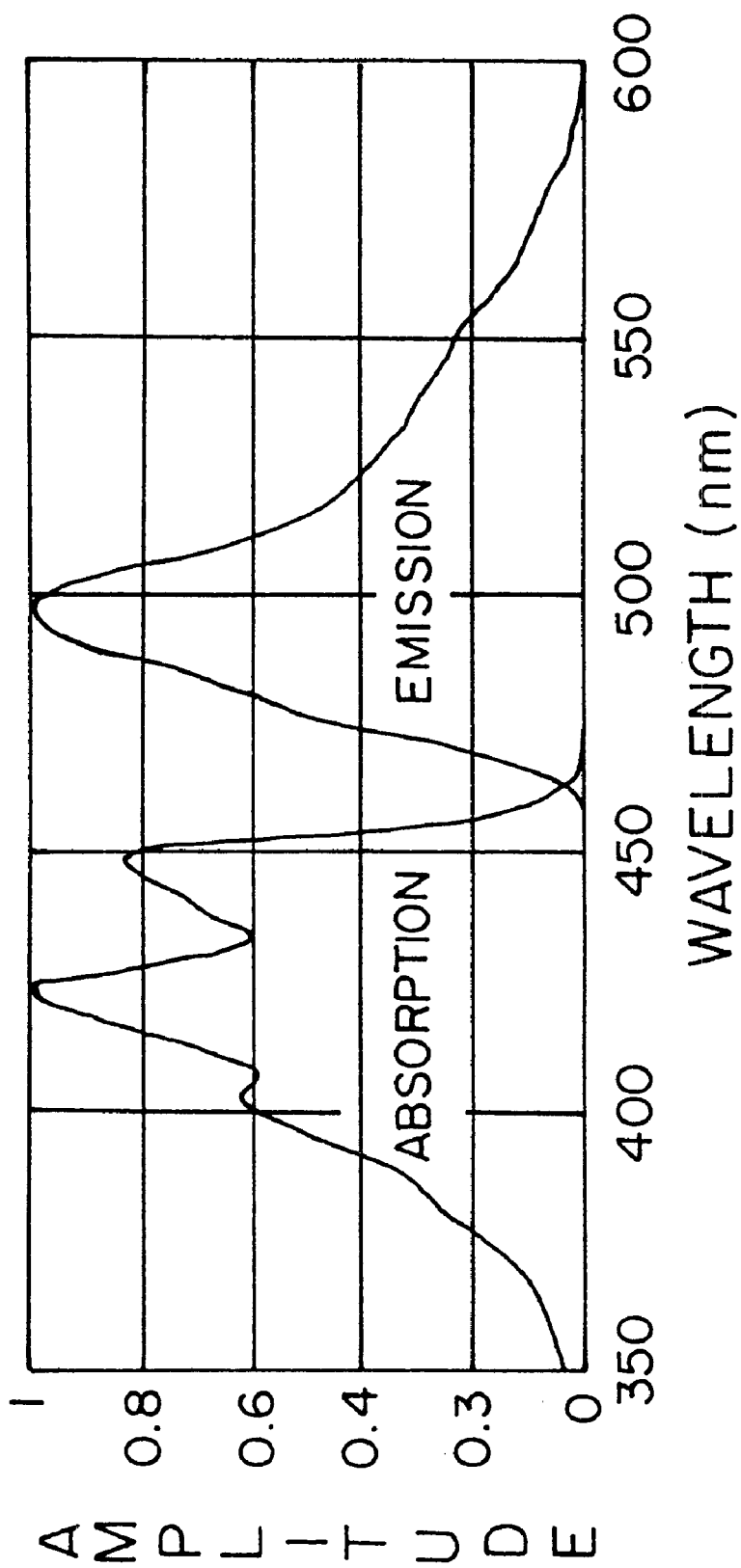
FIG. 5 illustrates emission and absorption spectra of a Bicron BCF-91A WLS fiber.
Figure 7:
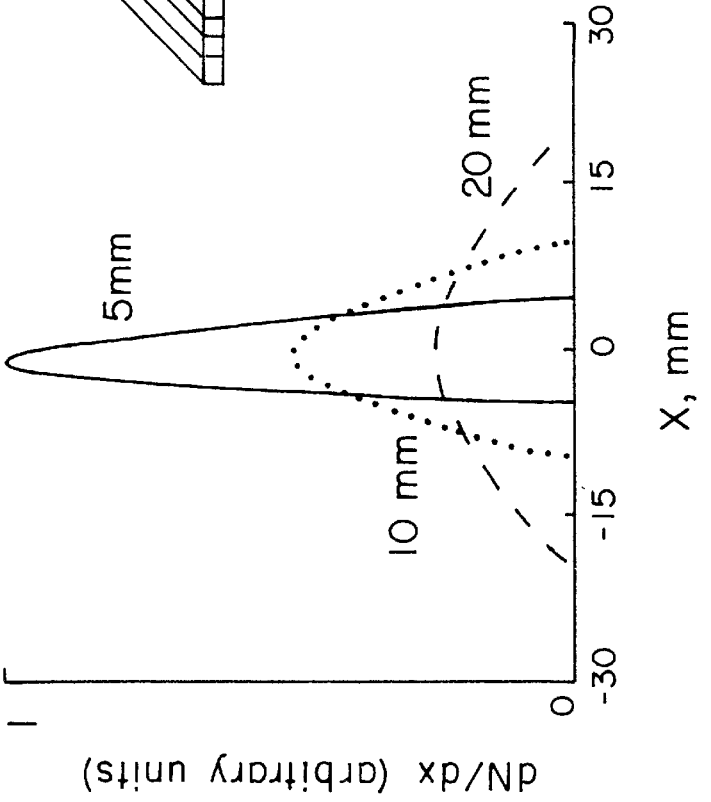
FIG. 7 illustrates theoretical light distribution profiles incident on wavelength-shifting fibers from several depths of interaction.

In the case of using NaI(Tl) as the scintillation crystal 18, for a fixed amount of absorbed energy, the number of scintillation photons within this light-exit cone 30 is about 20% of the total emitted photons, regardless of the DOI of the gamma ray 24. However, depending on the DOI of the gamma ray 24, the same number of photons will illuminate different sizes of circular areas on the WLS fibers 12, as illustrated in FIG. 5. A shallow DOI illuminates only a small area having a few of the fibers 32 of the WLS fibers 12. Conversely, a deeper DOI illuminates more of each of the fibers 32 in a larger area. As shown in FIGS. 8A and 8B, the photons are input to the WLS fiber 12 and cause photoscintillation with the resulting photons detected by the photosensor 33. The resulting intensity of distribution has useful information about DOI of the gamma ray 24. Therefore, the area of the WLS fibers 12 illuminated by scintillation photons contains important DOI information. An optical model leads to an analytical expression that predicts the distribution of scintillation photons reaching each of the fibers 32. The model assumes a relatively smooth interface between the scintillator crystal 18 and the fibers 32. The glass entrance window 16 which has approximately the same index of refraction as the cladding of the WLS fibers 12, will not affect the prediction significantly. Assume that K photons are emitted isotropically at point [0,0,z], where z is the DOI for the gamma ray 24. The number of photons transmitted to the fibers 32 in a rectangular area dxdy centered at [x,y,0] is given by $$\frac{d^2}{dxdy}N(x,y;z) = \frac{Kz}{4\pi}\frac{T(x,y;z)}{(x^2+y^2+z^2)^{3/2}} \quad (1)$$

where T(x,y,z) is the Fresnel transmission coefficient. The distribution of incident photons along each of the fibers 32 is obtained by integrating along the lengths of the fibers 32. If the fibers 32 are oriented along the y-axis, then $$\frac{d}{dx}N(x;z) = \frac{Kz}{2\pi}\int_0^{\sqrt{z^2\tan^2\theta_c - x^2}} dy \frac{T(x,y;z)}{(x^2+y^2+z^2)^{3/2}} \quad (2)$$

where $\theta_c$ is the critical angle. Both equations already indicate that the properties (e.g., width, peak amplitude) of the distribution will depend on the DOI of the gamma ray 24. FIG. 7 plots dN/dx for $\theta_c = 54°$ and three example DOIs: 5, 10, and 20 mm. The corresponding FWHMs of these profiles are 6.6, 13.2, and 26.4 mm, respectively. Thus, our model predicts a direct relationship between DOI of the gamma ray 24 and the width of the distribution of light in the WLS fibers 12. Solutions to these equations are readily obtainable by conventional numerical integration methodologies using a computer to execute a numerical integration program.

These profiles of FIG. 6 are characterized by convex shape and finite width. Shallow DOI for the gamma ray 24 produces a narrow profile, whereas deep DOI for the gamma ray 24 produces a wider, flatter profile. Note that the edges of the theoretical profiles drop to zero rather sharply. In reality, three secondary factors will blur the profiles' edges. These factors are: 1) other blue photons emitted outside the exit cone 30 could reach the WLS fibers 12 after one or more reflections from faces of the crystal 18; 2) the crystal 18 glass entrance interface is not perfect—the ideal expectations for refraction and reflection may not be strictly followed; and 3) the low transmission efficiency of the WLS fibers 12 results in high Poisson statistical noise. The first two factors are small in magnitude relative to the light contained within the light-exit cone 30. Their effects will spread over a wide spatial range and add a low spatial frequency component to the primary profile shown above. The third factor, present in all scintillation detectors, is especially important for a fiber-based detection system.

In a most preferred form of this invention, shown in FIG. 3 with exploded components, the scintillator crystal 18 is encased in an aluminum housing 34 with the glass entrance window 16 and the exit window 20. The rear half of the imaging system 10 comprising the scintillator crystal 18, the exit window 20 and the light sensor array 22, is unchanged from conventional Anger camera designs. The entrance window 16 is coupled optically to a ribbon of the WLS fibers 12, the entrance window 16 prevents the individual fibers 30 from conducting moisture to the hygroscopic crystal 18. The WLS fibers 12 could be oriented parallel to the longer axis of a rectangular form of the sensor array 22, minimizing the number of the fibers 30 and separate photosensors required to cover the detector face. The side of the WLS fibers 12 opposite the entrance window 16 is coated with reflecting powder 36. One end of each of the fibers 30 is coupled to a reflector 38 while the other end is coupled to the sensor array 33. The sensors array 22 can, for example, be multianode PMTs, avalanche photodiodes, conventional spiral shaped multiplier collectors, CCD's, or an array of conventional PMTs. In one form of the system 10 an array of green-sensitive PMTs can be used. Triggered by an energy signal of the main PMT array 22 of the Anger camera, an analog-digital converter (ADC) digitizes the output signals of the photosensor array 33 for real-crystal-fiber-reflector assembly can be encased in another aluminum housing for mechanical protection.

Note that all the other components and functions of the Anger camera remain intact. The main PMT sensory array 22 still performs the conventional operations of two dimensional (transverse and longitudinal or x and y) position sensing, energy discrimination and timing. The WLS fibers 12 provide supplemental DOI information for the detected gamma ray 24. One might expect that the Anger camera's conventional operation would be adversely affected because any light absorbed by the scintillating fibers is lost to the conventional portion of the Anger camera. This loss will however be small because only about 20% of the blue scintillation photons (mean wavelength of 420 nm) generated in the scintillator crystal 18 can get out of the crystal 18 to reach the fibers 32. Of the blue photons incident on the WLS fibers 12, 80% would be absorbed by the core of the fibers 30, with a 60% reemission at a longer wavelength (mean of 500 nm) as green photons. With the reflector 38 coating the front of the WLS fibers 12, any transmitted blue photons will be reflected locally and have a second chance to interact with the WLS fibers 12. A small fraction of the green photons undergo total internal reflection in the fiber and propagate down each of the fibers 32 to the outside photosensor array 33. The remaining wavelength-shifted green photons and unabsorbed blue photons pass back into the crystal 18 and some of them may eventually exit the rear window to reach the main sensor array 22. The green and blue photons that reach the sensor array 22 can contribute to the conventional x,y position and energy determination, although conventional PMTs are generally less sensitive to green light than blue light. Because we preferably use the WLS fibers 12 only on the entrance side, the PMT sensor array 22 will not be masked by the fibers 32, our light collection is more favorable, so we have relatively small loss in total light output and energy resolution.

Because the amount of light transmitted to the fibers' ends is extremely low, all of the components in the light transmission chain should be optimized to achieve the most reliable detection. To optimize light output from the WLS fibers 12, the ends of the fibers 32 opposite the photosensor array 33 are polished and coupled most preferably to a reflective mirror surface 35, such as a piece of aluminized mylar film. This reflecting technique can nearly double the light collection efficiency of the WLS fibers 12.

The sensor array 22 also preferably is capable of measuring low intensity green light down to single photoelectron (PE) levels. At this time, PMTs are the most suitable for detecting single PEs because of their exceedingly high gain factor. Although commercially available Si-based avalanche photodiodes (Si-APDs) have much higher quantum efficiency (QE) than PMTs for green light, they are not capable of room-temperature operation at extremely low-light levels. At this time, there is also active development of new high-gain short-wavelength APDs that are capable of single PE detection at room temperature. When these APDs become commercially available, they would be an advantageous sensor array 22 of choice. In this most preferred current embodiment, single-anode green-sensitive PMTs, such as Photonis' XP3461B that has a QE of 25% at 500 nm. For future large-scale implementation, green-sensitive position sensitive PMTs (PSPMTs) might be useful.

Figure 9:
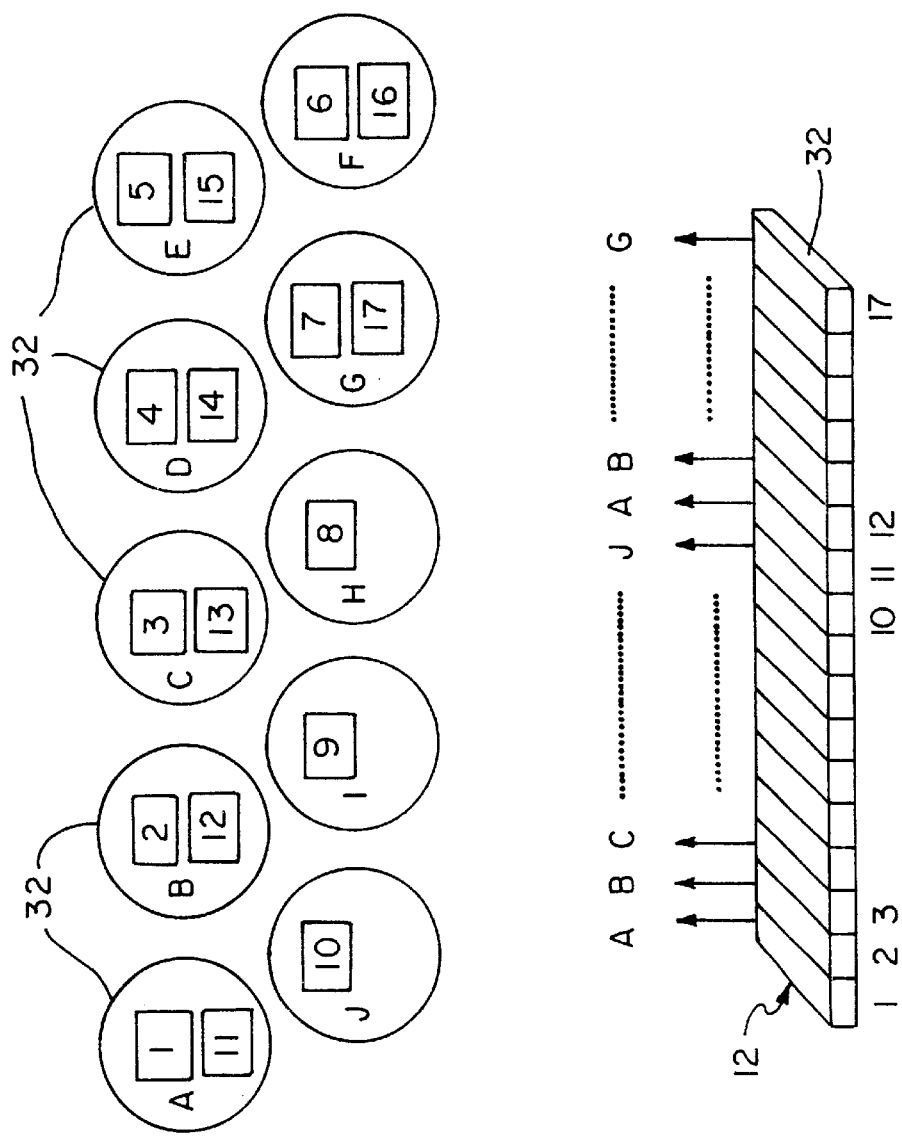
FIG. 9 illustrates a photosensor array sharing approach for a bundle of wavelength shifting fibers.

Another alternative for reading out large numbers of the fibers 32 is to use conventional PMTs in a sharing scheme as illustrated in FIG. 9. Assuming the fibers 30 in the WLS fibers 12 are grouped in bundles to improve light output, adjacent ones of the bundles 38 (e.g., bundles 38a and 39b) are coupled to separate sensors of the array 22. Two bundles which are spatially distant from each other, such as bundles 38a and 38b, can be coupled to the same PMT; both of these bundles 38a and 38b cannot produce signals from the same event if one of the bundles 38 is far from the light-exit cone 30 (see FIG. 6). The number of PMTs required by this sequential, cyclical sharing scheme is determined by the maximum area illuminated by a gamma ray interaction at the deepest depth in the crystal 18 and the number of the fibers 32 for the bundle 38. This PMT-sharing scheme works for the readout of fiber signals because the fibers 32 are used only to determine the width of the light distribution and the crystal thickness places an upper limit on the diameter of the light-exist cone 30 at the WLS fibers 12. A PMT-sharing scheme has several notable advantages. These include using green-sensitive PMTs, using off-the-self components (pre-amps, amplifiers, etc.) and the lower cost of 10–12 conventional PMTs compared to one position-sensitive PMT.

The overall efficiency of the fiber-based system 10 will also affect the precision of measuring DOI for the gamma ray 24 during positron coincidence imaging with dual-head Anger cameras. The following is not meant to be limiting to the invention, but merely an example of estimates of the efficiency of each stage involve in generating PEs in the photosensors 33 from scintillation photons in the crystal 18. The overall efficiency is the product of these factors.

$\Omega$=geometric efficiency;$\Omega$=(½)*(1-cos $\theta_c$),$\theta_c$=54°=0.2

$f$=effective packing fraction of the multi-clad square fibers' scintillating cores=0.95

$\epsilon$=efficiency for wavelength shifting from 420 nm to 500 nm=0.5

$\eta$=fraction of green light transmitted through the fiber (trapping efficiency)=0.073

$\mu$=average attenuation of 550 nm photon through a 100 cm length of fiber=0.85

$\tau$=efficiency of reflection from the mirrored end of the fiber=1.85

$\chi$=second chance of absorption of blue photons due to detector's reflective coating=1.19

$\sigma$=optical coupling losses at the PMT's entrance window=0.9

$\lambda$=the quantum efficiency of green-sensitive PMTs for 500 nm green light=0.25

Combining all of these factors, the overall efficiency is 0.3%. The values for these factors were obtained from the WLS fiber vendor [Bicron, 1999], computed from simple geometric models and estimated based on experience with scintillation detector systems. Trapping efficiency is the major limiting factor, allowing only internally reflected light to be transmitted through the fiber 32.

On average, 26 eV deposited in crystal 18 generates one scintillation photon; thus the average yields of PEs are for a 511 keV photon, (511 keV /26 eV) x0.3% =59 PEs for a 140 keV photon, (140 keV /26 eV) x0.3% =16 PEs These are the estimated mean total number of PEs created by all of the fibers 32 in the PMTs' photocathodes following a complete photoelectric absorption. These PEs are spread over a quantity of the fibers 32 that depends on the DOI of the gamma ray 24. By bundling several of the fibers 32 together (described hereinbefore), the signal-to-noise ratio can be increased. The number of the fibers 32 per bundle 38 is one of the optimization tasks proposed for this feasibility study. For instance, for a 2.0 cm DOI the base of the light-exit cone 30 will be 6 cm in diameter, covering sixty 1-mm wide fibers 32; a 0.5 cm DOI would illuminate fifteen of the fibers 32. With six fibers per bundle 38, this would correspond to 10 and 2.5 bundles 38, respectively, as illustrated in FIG. 9. The statistical variation in the total number of PEs in the WLS fibers 12 should strictly follow Poisson statistics. The distribution of PEs among the fibers bundles 38 is our primary interest. The width of the distribution, and hence the DOI of the gamma ray 24, is determined from the number of PEs produced by each of the fiber bundles 38. Of particular importance is the sensitivity and reproducibility for low-level light detection at the edges of the light distribution, where the number of PEs in the bundle 38 is very small. Thus the precision of the DOI measurement will be determined largely by the detection efficiency of the photosensors at very low light levels.

An estimate for the yield of PEs in the scintillating fibers 32 agrees reasonably with recently reported experimental results, allowing for differences in experimental designs. Our quantitatively greater PE yield results primarily from the higher trapping efficiency of the multi-clad square fibers 32 (Bicron BCF-91A), which is more than twice that of a single-clad form of round fibers 32. Additional significant improvements to PE yield are due to the high light output of crystal 18 and the high quantum efficiency of green-sensitive PMTs (such as photon is XP3457B) to the wavelength-shifted light from the WLS fibers 12. The use of the reflectors 35 to optimize light collection provides further improvement.

The above-described methods for correcting nuclear images for DOI effects can generally be applied to conventional nuclear imaging systems which use only a single gamma ray set to image patient information. Regardless of the type of gamma radiation used or the type of system, if there is error introduced by assumptions about DOI, the invention can be applied advantageously. Therefore, the system 10 illustrated by FIG. 3 can include either one or two such assemblages, but the correction for DOI effects as described herein can be used to advantage in any system formed from any type of radiation which introduces error arising from improper assumptions about DOI effects.

Figure 4:
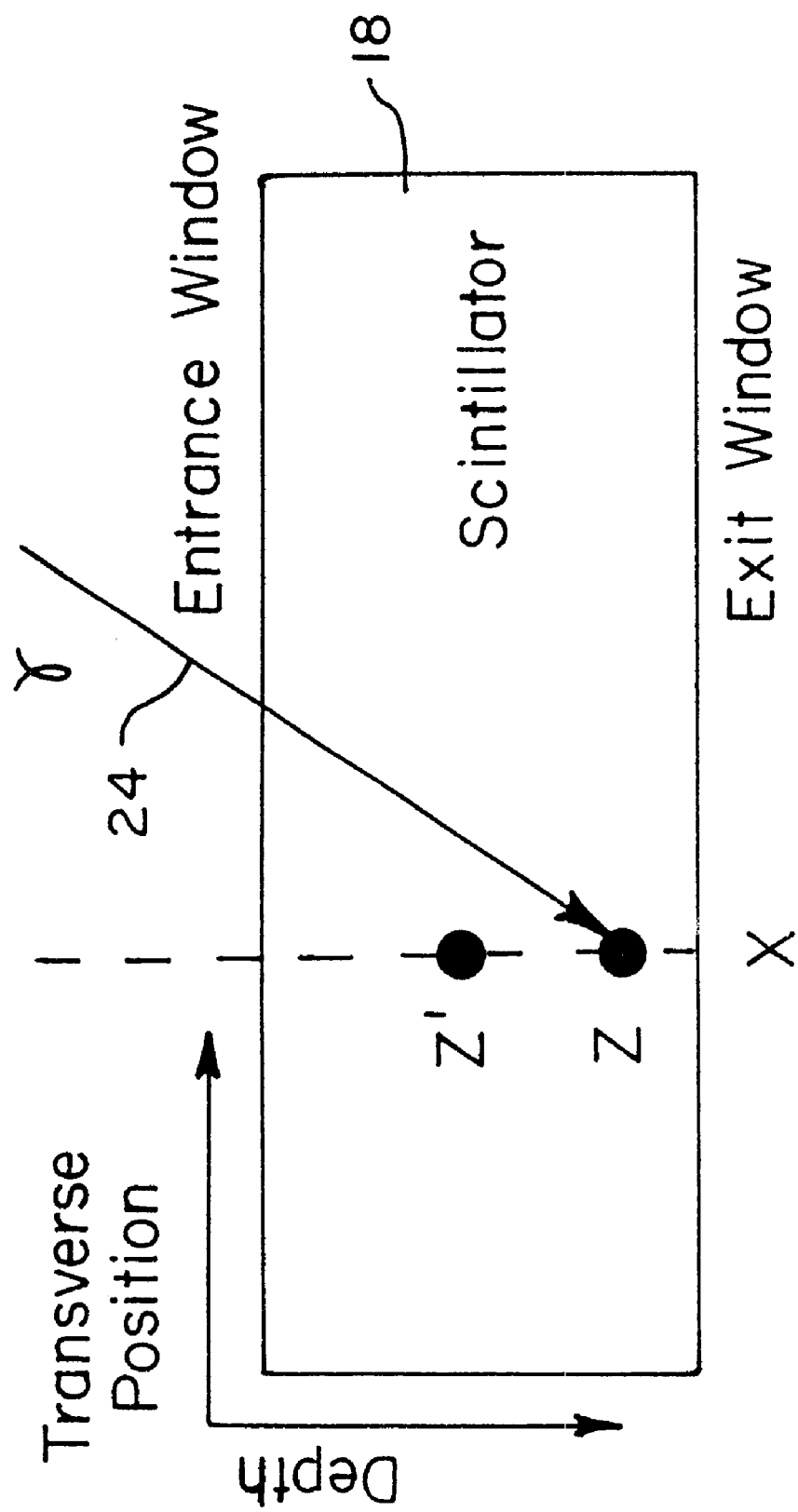
FIG. 4 illustrates a partial section of a scintillation crystal and gamma ray interacting at a given depth.

In yet another aspect of the invention an analytical methodology has been developed to correct for the DOI for the gamma ray 24 shown in FIG. 4. A general approach to this DOI correction can be understood by referring to FIG. 10 which shows the most general configuration for two identical scintillator crystals 40 and 42 designed to detect, in coincidence, pairs of 511-keV gamma rays 44 emitted after positron-electron annihilation events occurring within a patient to be imaged. With suitable choices for the detector dimensions (length L and thickness T) and angular separation ($\alpha$), the geometries of most existing PET systems can be described. In particular, the choice $\alpha=\pi$ corresponds to coincidence detection with dual-Anger cameras (see FIG. 1 for a prior art single gamma camera system).

Figure 1:
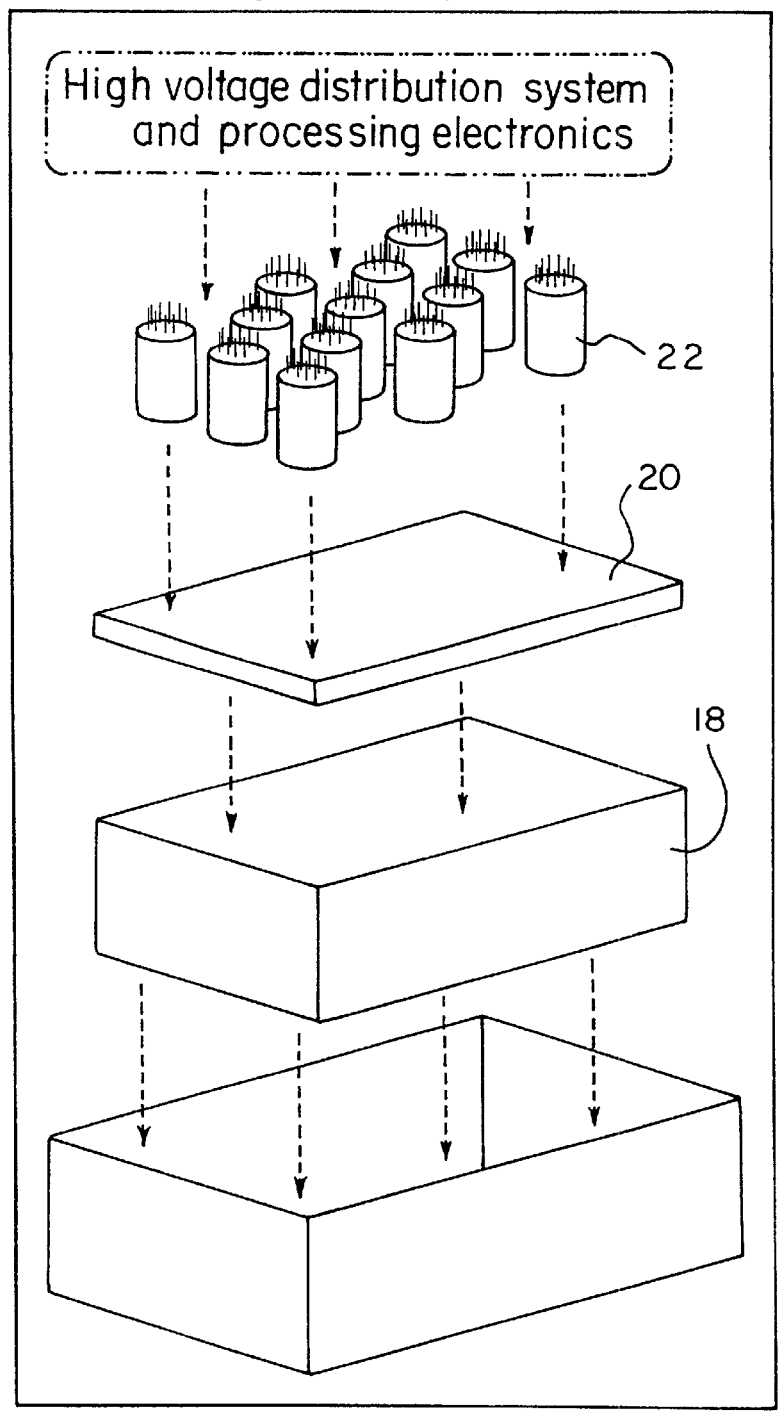
FIG. 1 illustrates a prior art gamma camera system with exploded components.

In the prior art single gamma camera system shown in FIG. 1: the processing electronics connect to the PMT array and an external acquisition computer; the PMT array is optically bonded to the glass exit window and typically has 70–120 PNTs; a glass exit window is optically bonded to the PMT array and the NaI(TI); the backf ace of the NaI(TI) scintillation crystal is bonded optically to the PMT array; the front face is coated with reflective powder; a 5-sided protective aluminum scintillator housing surrounds the NaI(TI) crystal and is hermetically sealed to the edges of the glass exit window; and the entire assembly is housed within a radiation- shielded camera enclosure. Note: vertical dimensions are exaggerated and not to scale.

Figure 2:
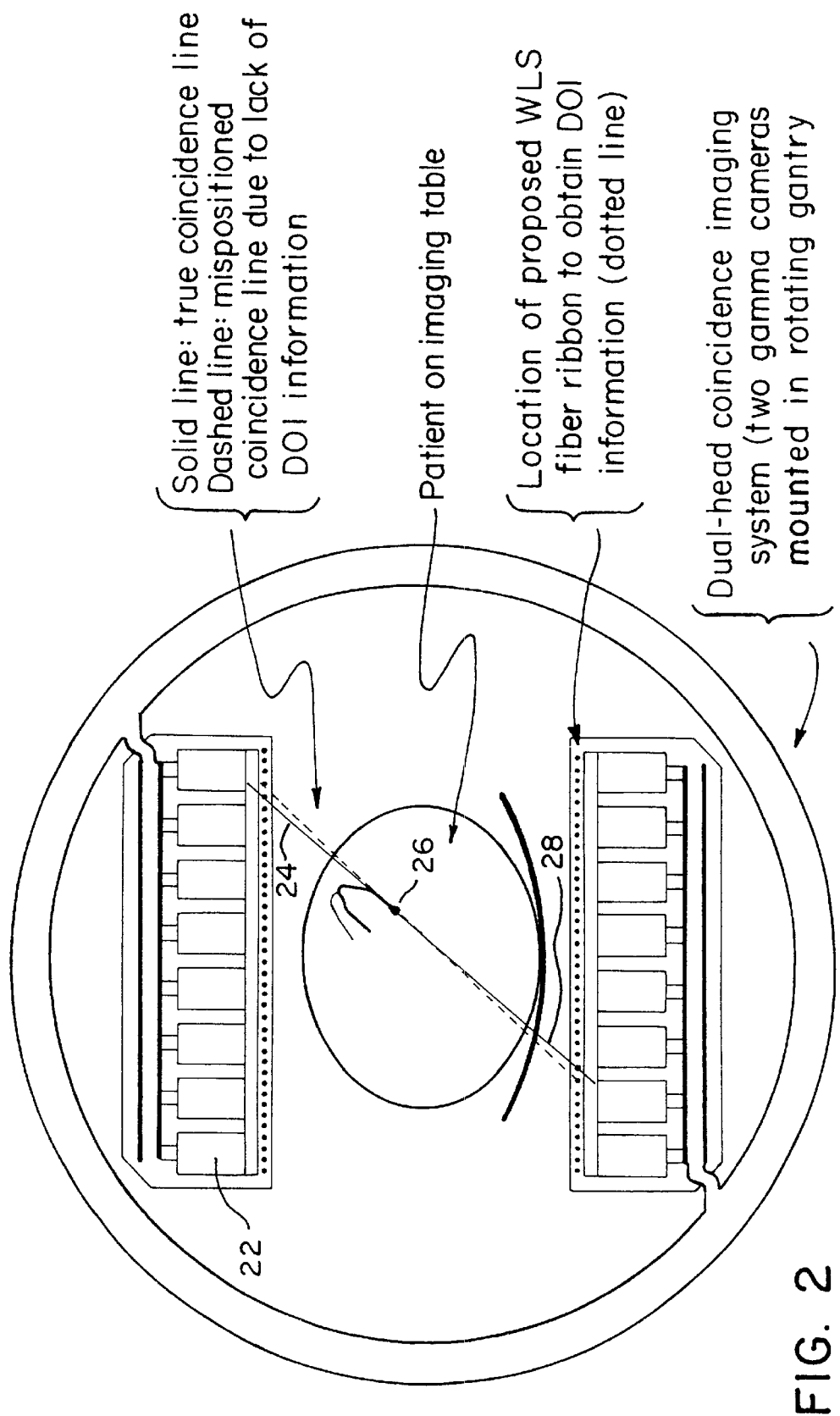
FIG. 2 illustrates a dual-head gamma camera system.

The analysis to follow applies to bar detectors, such as found in single-slice type of PET systems (see FIG. 2). However, similar analysis can be easily applied to planar detectors.

Figure 10:
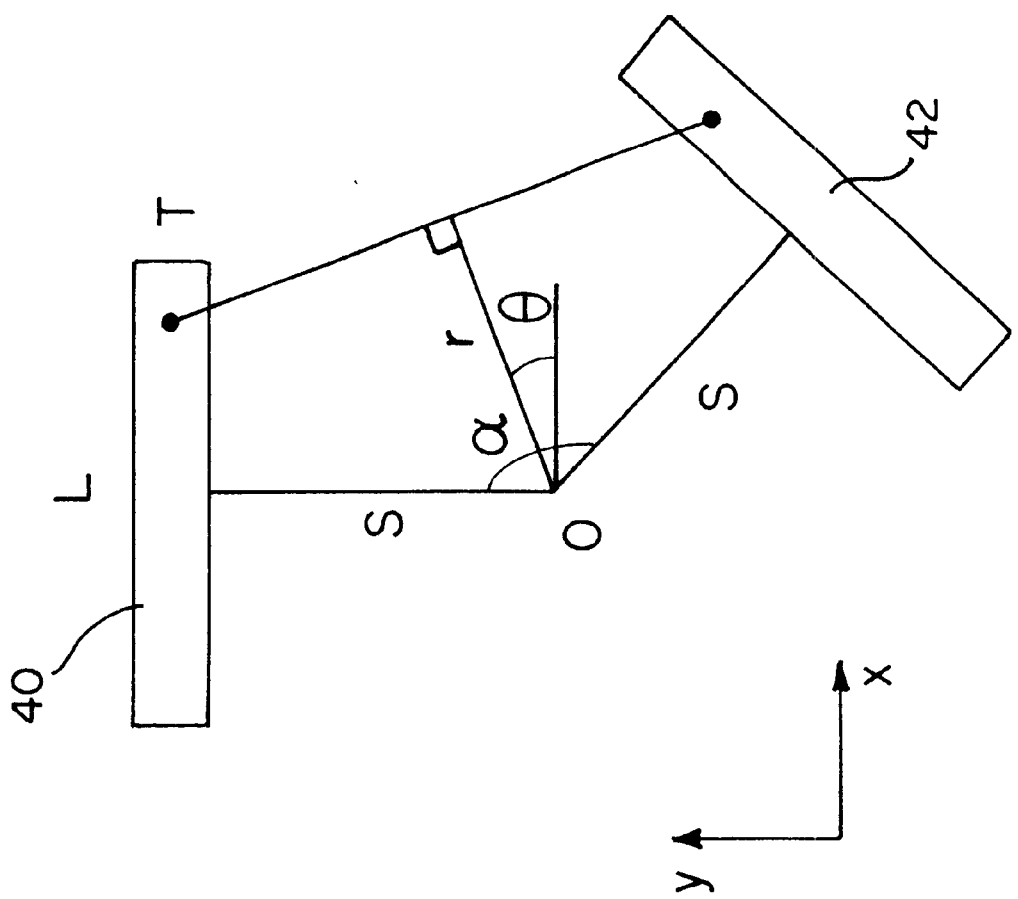
FIG. 10 shows a general configuration of two scintillators for detecting coincidence pairs of gamma rays.

A coincidence event is shown in FIG. 10 as a line connecting two interaction positions observed in the two separate scintillator crystals 40 and 42. These positions, denoted by solid circles, are measured with respect to a fixed (laboratory) frame centered at O. Let $\{x_1, y_1\}$ and $\{x_2, y_2\}$ denote the laboratory-frame coordinates of the interaction positions in the crystals 40 and 42, respectively. Image reconstruction of coincidence data is carried more conveniently after a coordinate transformation of the interaction positions $\{x_1, y_1, x_2, y_2\}$. This transformation, referred to as rebinning, results in two new variables, $$\theta = \tan^{-1}\left(-\frac{x_2 - x_1}{y_2 - y_1}\right) \quad (3)$$

$$r = (x_1 \cos\theta + y_1 \sin\theta) \quad (4)$$

that characterize completely each coincidence event: $\theta$ measures the angular offset of the event from a fixed reference axis, and r is the (signed) distance of the coincidence line from the laboratory-frame origin. Clearly, the accuracy of the calculation of the sinogram variables depends on the accuracy with which the interaction positions are measured.

In actual applications, the interaction positions are measured with respect to each detector's local reference frame. For each of the crystals 40 and 42, choose the origin of such frame to be at the detector's geometric center. In addition, make the frame's X-axis and Y-axis to be parallel to the length and depth of the crystal (40 or 42), respectively. Thus, the transverse positions and DOI in each of the crystals 40 and 42 will have values $|X| \leq \frac{1}{2}L$ and $|Y| \leq \frac{1}{2}T$, respectively.

Let $\{X_1, Y_1\}$ and $\{X_2, Y_2\}$ denote the interaction positions in terms of detector coordinates in the crystals 40 and 42, respectively. The transformation from detector coordinates to laboratory coordinates, for use in (3) and (4), is given by the following:

$$x_1 = X_1 \quad (5)$$

$$y_1 = \tfrac{1}{2}H + Y_1 \quad (6)$$

$$x_2 = \left(\tfrac{1}{2}H + Y_2\right)\sin\alpha + X_2\cos\alpha \quad (7)$$

$$y_2 = \left(\tfrac{1}{2}H + Y_2\right)\cos\alpha - X_2\sin\alpha \quad (8)$$

Where H=2S+T. Note that (7) and (8) represent a simple translation from the local frame of the crystal 40 to the laboratory frame. Note also that (7) and (8) are related to (5) and (6) via a rotation transformation. The sinogram variables in terms of the measured detector coordinates are then given.

Let us assume that the crystals 40 and 42 are capable of independent measurement of the transverse positions $\{X_1, X_2\}$ and DOIs $\{Y_1, Y_2\}$ that appear in (5)–(8). The uncertainties ($\Delta X, \Delta Y$) in the measurement of X and Y are related to the spatial resolutions along the length and depth of each of the crystals 40 and 42, respectively. Consequently, the uncertainties in the calculation of r and $\theta$ will depend on $\Delta X_1, \Delta Y_1, \Delta X_2$, and $\Delta Y_2$. Furthermore, $\Delta X_1 \approx \Delta X_2 \equiv \Delta X$ and $\Delta Y_1 \approx \Delta Y_2 \equiv \Delta Y$ because the two crystals 40 and 42 are assumed to be identical.

With the use of elementary error analysis, the uncertainties $\Delta r$ and $\Delta\theta$ in terms of $\Delta X$ and $\Delta Y$ for arbitrary $\alpha$ can be derived straightforwardly. Here, we present only the results for $\alpha = \pi$ (parallel detectors, as in dual-Anger cameras for coincidence imaging). Specifically, $$[\Delta\theta]^2 = \frac{2}{\left[H^2 + (\overline{X}_1 + \overline{X}_2)^2\right]^2}\{[H\Delta X]^2 + [(\overline{X}_1 + \overline{X}_2)\Delta Y]^2\} \quad (9)$$

$$[\Delta r]^2 = \frac{H^4 + 2(\overline{X}_1 + \overline{X}_2)^2(H^2 + \overline{X}_1^2 + \overline{X}_2^2)}{2[H^2 + (\overline{X}_1 + \overline{X}_2)^2]^3}\{[H\Delta X]^2 + [(\overline{X}_1 + \overline{X}_2)\Delta Y]^2\} \quad (10)$$

The over-bars in (9) and (10) indicate that the mean values of the corresponding variables must be used. In arriving at (9) and (10), we have used the approximation $\overline{Y}_1 = \overline{Y}_2 = 0$, or that the mean DOI of the gamma ray 44 is at half-crystal thickness. This approximation is very good for 511 keV gamma rays when the thickness of the scintillator crystal 18 is small compared to the distance between the two crystals 40 and 42.

The uncertainties (9) and (10) have use even if DOI is not measured—as is true for nearly (if not) all PET systems. In this case, the uncertainty in the DOI is approximately given by the thickness of the crystal (40 and 42): $\Delta Y \approx T$. Thus, the uncertainties are at their worst and one obtains upper limits to the angular and position resolutions ($\Delta\theta_{max}$ and $\Delta r_{max}$, respectively). Clearly, these resolutions are worse for thicker detectors. Conversely, the resolutions improve if DOI were measured with accuracy $\Delta Y < T$. The effects of DOI disappear altogether if DOI were measured precisely, $\Delta Y = 0$.

The general behavior of $\Delta r$ and $\Delta\theta$ can be elucidated by considering two extreme cases.

A. Normal Incidence

When $\overline{X}_1 = -\overline{X}_2$, the coincidence line is perpendicular to both of the crystals 40 and 42; (9) and (10) reduce to $$\Delta\theta = \sqrt{2}\,\frac{\Delta X}{H} \quad (11)$$

$$\Delta r = \frac{\Delta X}{\sqrt{2}} \quad (12)$$

Thus, as expected, the uncertainties $\Delta r$ and $\Delta\theta$ depend on the transverse spatial resolution only.

B. Oblique Incidence The coincidence line is oblique to both of the crystals 40 and 42 when $\overline{X}_1 \neq -\overline{X}_2$. The most oblique incidence occurs when $\overline{X}_1 \overline{X}_2 = \pm\frac{1}{2}L$. In either case, $$[\Delta\theta]^2 = \frac{2}{[H^2 + L^2]^2}\{[H\Delta X]^2 + [L\Delta Y]^2\} \quad (13)$$

$$[\Delta r]^2 = \frac{H^4 + L^2(2H^2 + L^2)}{2[H^2 + L^2]^3}\{[H\Delta X]^2 + [L\Delta Y]^2\} \quad (14)$$

The effects of DOI on the resolutions are explicitly accounted for by the $[L\Delta Y]^2$ in (13) and (14).

The analytical dependence of the angular and position resolutions of PET projection are shown for the DOI of the gamma ray 44. The dependence of the latter (position resolution) on DOI has been recognized for a long time. However, the dependence of the angular resolution on DOI is surprising.

Hereinafter will be shown the magnitude of these effects with some numerical examples.

The relative effects due to the uncertainties in the measurement of transverse positions and the DOIs can be better elucidated if we first rewrite (9) and (10)—or (13) and (14)—as follows:

$$[\Delta\theta]^2 = k_{\theta,X}[\Delta X]^2 + k_{\theta,Y}[\Delta Y]^2 = [\Delta\theta_X]^2 + [\Delta\theta_Y]^2 \quad (15)$$

$$[\Delta r]^2 = k_{r,X}[\Delta X]^2 + k_{r,Y}[\Delta Y]^2 = [\Delta r_X]^2 + [\Delta r_Y]^2 \quad (16)$$

Whereas $\Delta X$ and $\Delta Y$ characterizes the measurement process, the constants k contain the contributions of detector configuration to the solutions. Thus, our equations are consistent with experimental observations that spatial resolution, at least depends on geometry.

Let us illustrate the magnitude of these effects via some numerical examples. Because the effects of DOI are more severe at oblique angles of coincidence, our examples will be limited to $\overline{X}_1 = \overline{X}_2 = \pm\frac{1}{2}L$ cases. The e following examples assume L=50 cm, T=2.5 cm (unless otherwise stated), and $\Delta X = 0.5$ cm. The dimensions of the scintillator crystals 40 and 42 roughly correspond to that of the modules of the PENN-PET. The chosen spatial resolution is also roughly the same as the intrinsic spatial resolution of the NaI(Tl) scintillator crystals of the PENN-PET.

A. Effect of Distance Between Detectors

The center-to-center distance of separation, H=2S+T, between the two scintillator crystals 18 can be changed depending on the object to be imaged. Let us consider the following choices: H=30 cm for brain imaging, and H=60 cm for body imaging. In each case, we want to calculate how the sinogram resolutions behave for different values of the DOI uncertainty.

Figure 11:
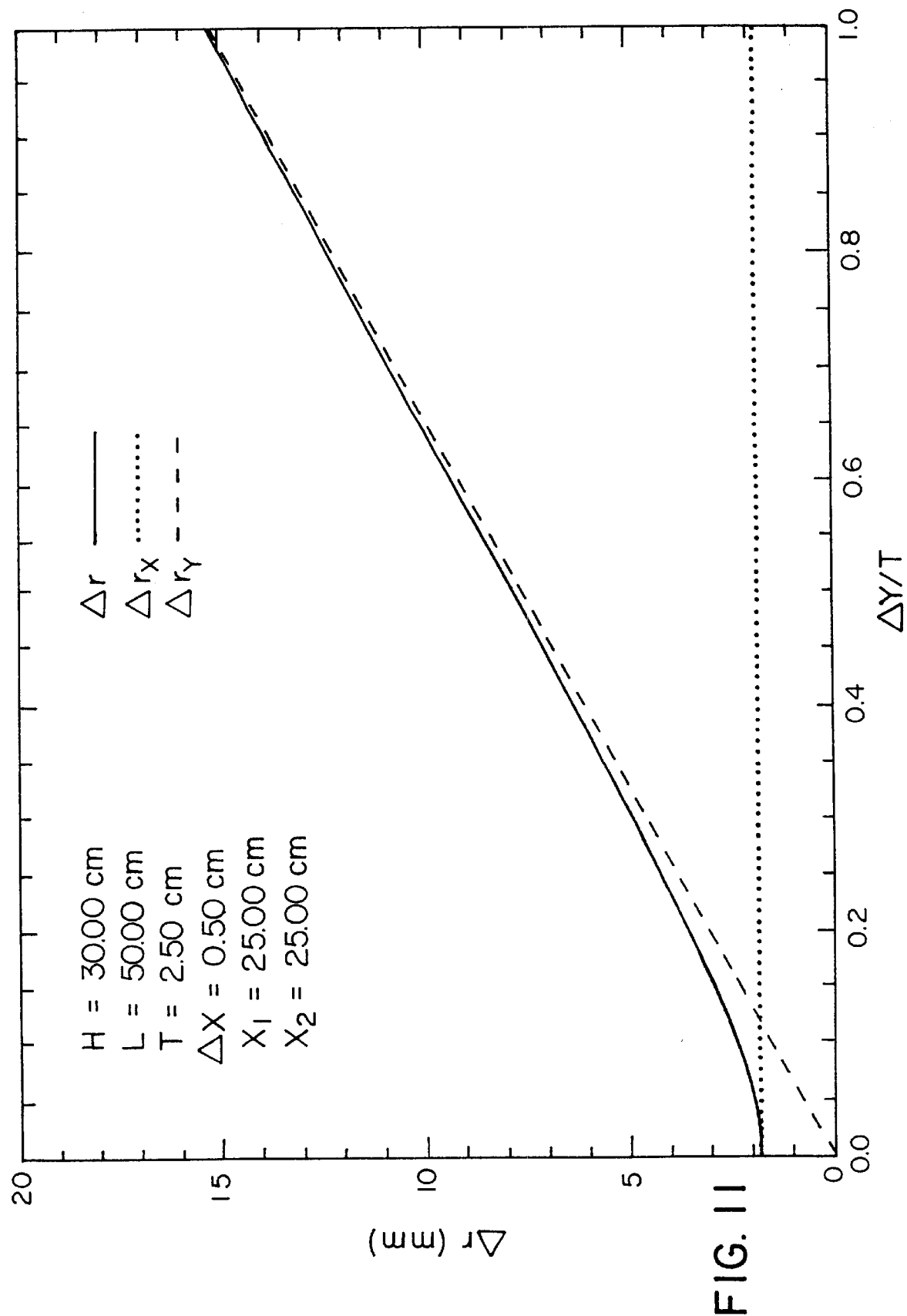
FIG. 11 shows effect of DOI uncertainty on intrinsic spatial resolution for brain imaging.
Figure 12:
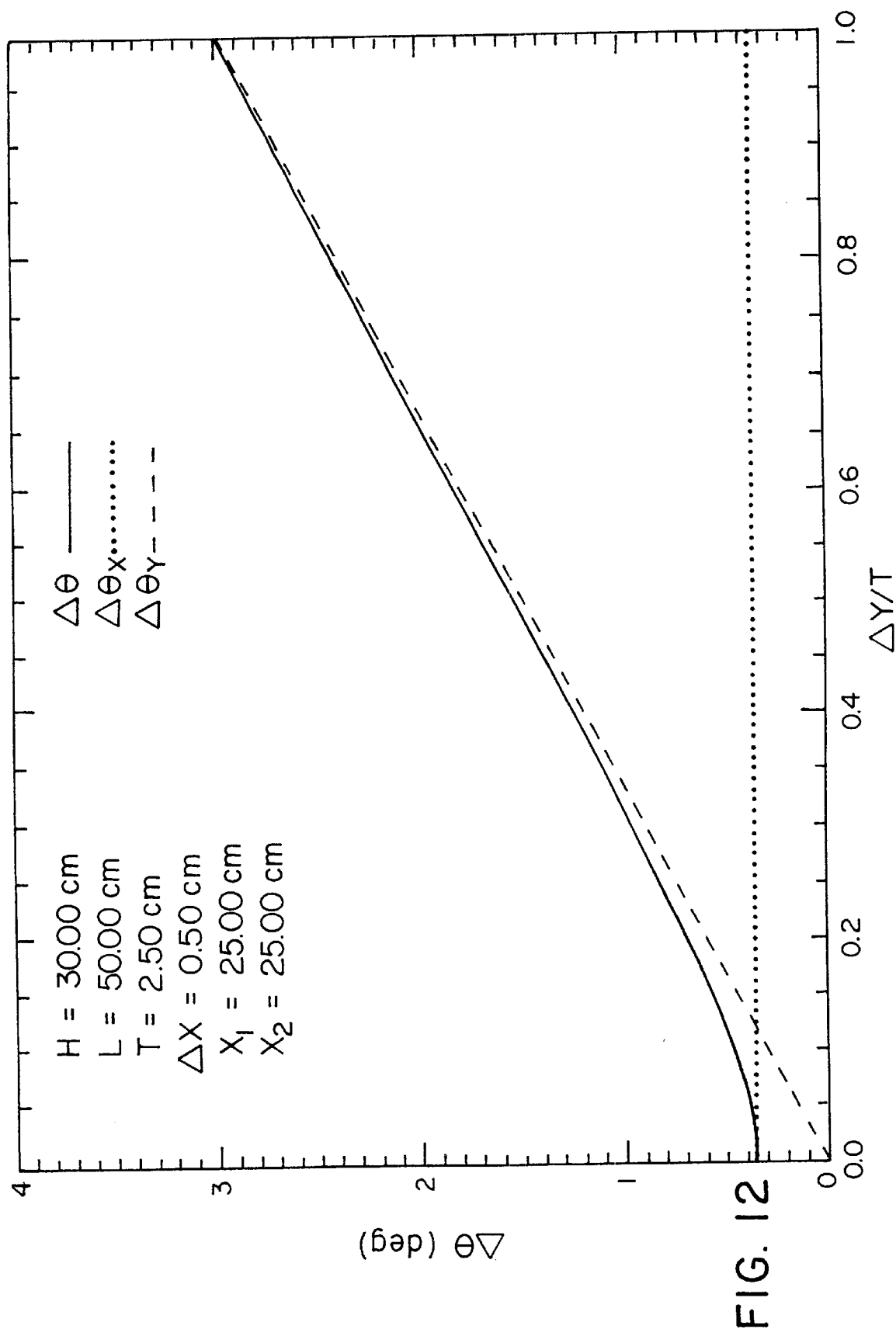
FIG. 12 shows effect of DOI uncertainty on angular resolution for brain imaging.

FIGS. 11 and 12 show the effects of the DOI uncertainty (expressed in terms of ΔY/T) on the position resolution and angular resolution, respectively, for H=30 cm. The dotted line in FIG. 11 (FIG. 12) corresponds to $\Delta r_x(\Delta\theta_x)$; the dashed line corresponds to $\Delta r_y(\Delta\theta_y)$. In both cases, the contribution from the transverse position is constant. ΔY/T=0 corresponds to perfect measurement of DOI. The maximum (worst) resolutions occur when ΔY/T=1, which corresponds to no DOI information at all. Note that at ΔY/T=0.5, which corresponds to measuring DOI within the front or back half of the crystal 40, the resolutions have improved by almost a factor of two.

Figure 13:
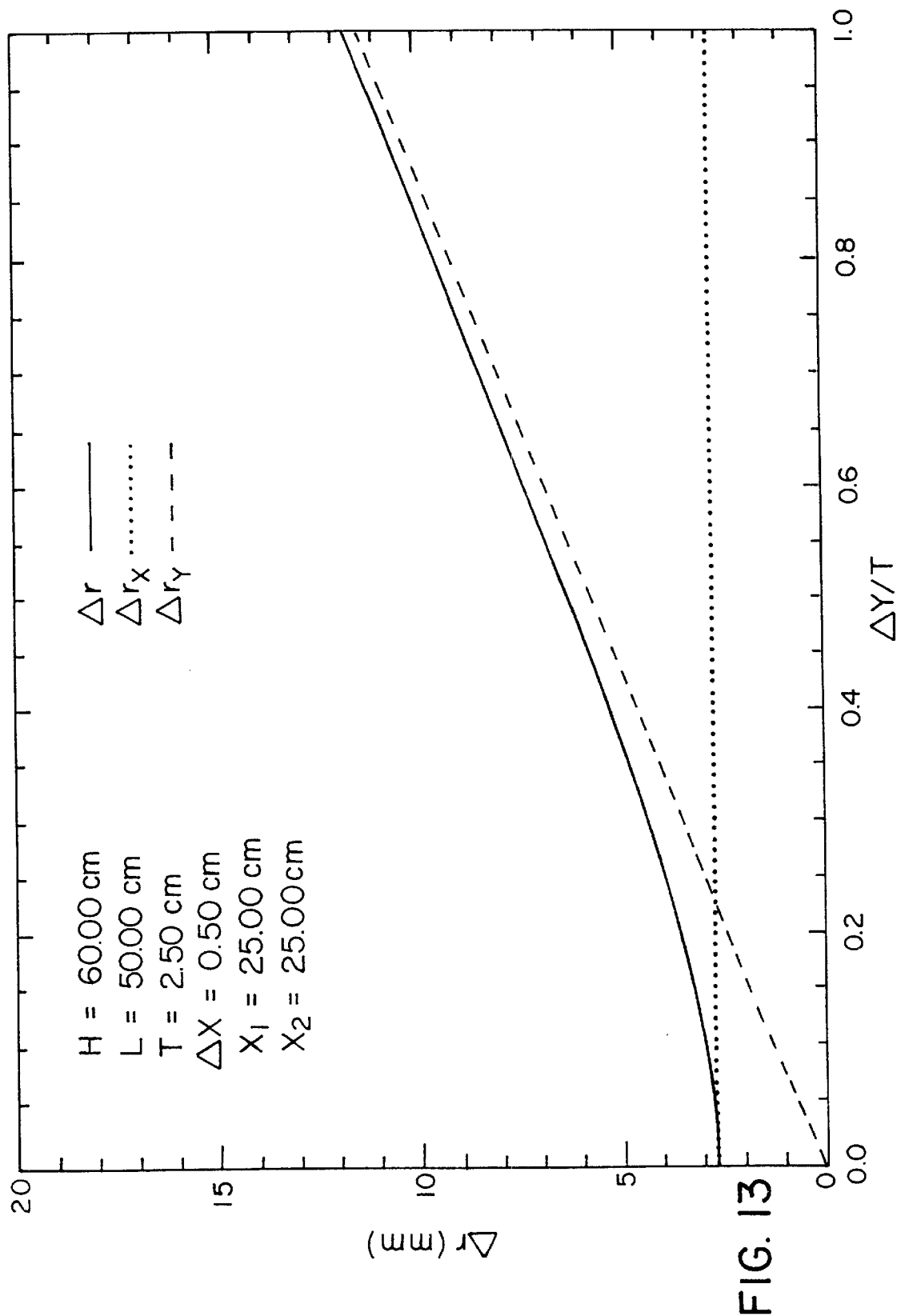
FIG. 13 shows effect of DOI uncertainty on intrinsic spatial resolution for body imaging.
Figure 14:
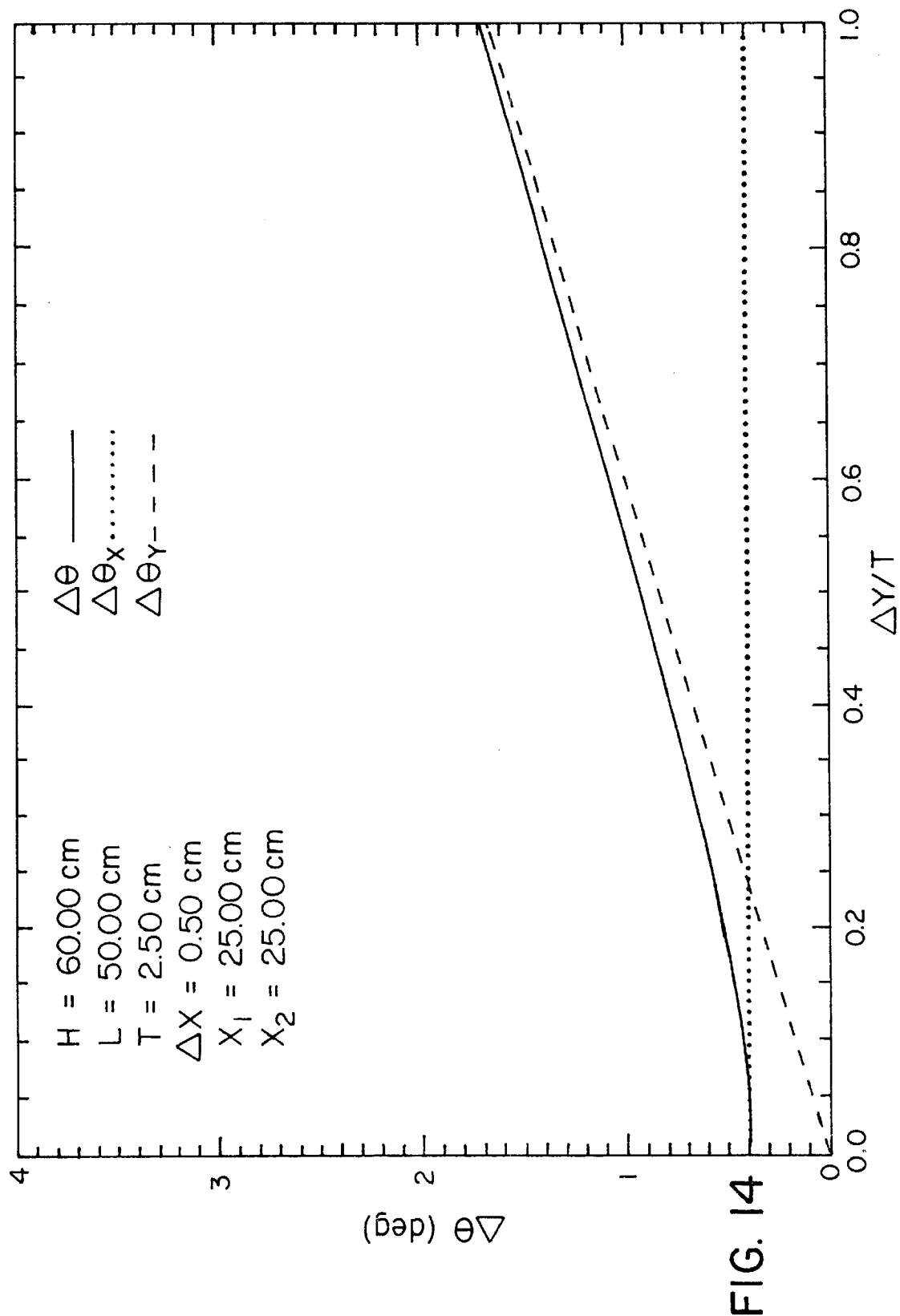
FIG. 14 shows effect of DOI uncertainty on angular resolution for body imaging.

FIGS. 13 and 14 are similar to FIGS. 11 and 12, but H=60 cm for body imaging.

Upon comparison of FIG. 11 with FIG. 13 (or FIG. 12 with FIG. 14), it is apparent that DOI effects are more prominent when crystals 40 and 42 are closer to each other. (This effect is observed when comparing ring PET systems with different diameters.) In particular, note that $\Delta r_x$ and $\Delta r_y$ are almost equal at about ΔY/T=0.12 for H=30 cm. For H=60 cm, the equality occurs at about ΔY/T=0.25. Thus, to minimize the effects of DOI (such that the more dominant contribution comes from the transverse intrinsic spatial resolution), one requires better (smaller) DOI resolution as the separation between the crystals 40 and 42 decreases.

B. Effect of Scintillator Crystal Thickness

Figure 15:
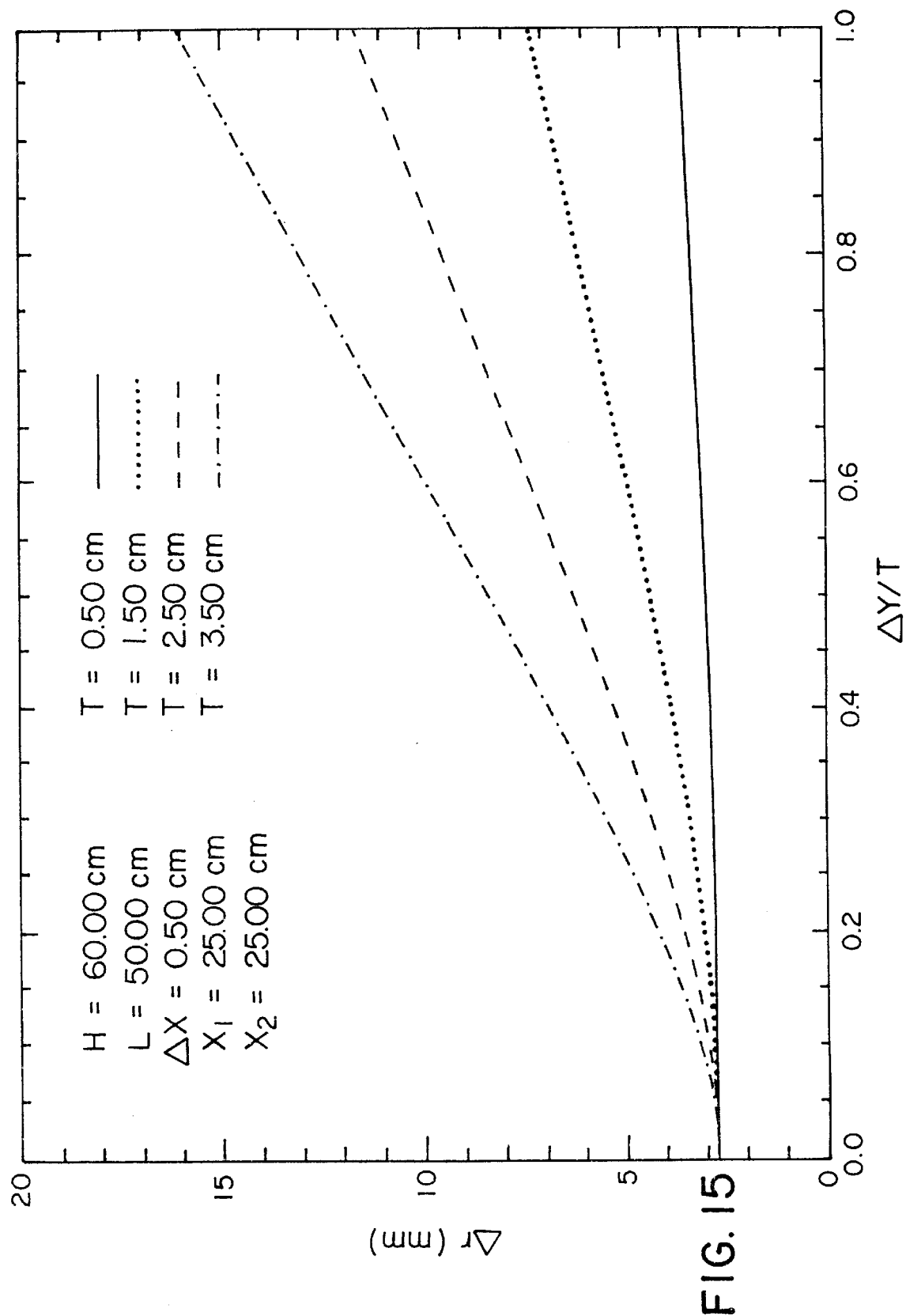
FIG. 15 shows the effect of crystal thickness on the intrinsic spatial resolution for body imaging.

FIG. 15 shows the effects of thickness on the position resolution ($\Delta r = \sqrt{[\Delta r_X]^2 + [\Delta r_Y]^2}$) for the following parameters: H=60 cm (for body imaging), L=50 cm, ΔX=0.5 cm, and $\overline{X}_1 = \overline{X}_2 = \pm\frac{1}{2}L$. The curves (top to bottom) in FIG. 15 correspond to thickness of 3.5, 2.5, 1.5, and 0.5 cm, respectively. For thin detectors, DOI has no significant effects. For example, for T=0.5 cm, the position resolution is practically constant for all possible values of the DOI resolution. This implies the position resolution is practically determined by the transverse intrinsic spatial resolution, and it does no good to measure the DOI separately. On the other hand, DOI effects dominate the position resolution for thicker detectors.

While preferred embodiments have been illustrated and described, it should be understood that changes and modifications can be made therein in accordance with one of ordinary skill in the art without departing from the invention in its broader aspects. Various features of the invention are defined in the following claims.

What is claimed is:

1. A system for determining an interaction site of a gamma ray in a scintillation crystal, comprising:
   a scintillation crystal for interacting with gamma radiation to emit photons, the interaction occurring at an interaction site within the scintillation crystal characterized by an x-position, a y-position and a depth of interaction;
   a first sensor array disposed on one side of said scintillation crystal to detect photons emitted from said scintillation crystal;
   a second sensor array disposed on another side of said scintillation crystal, opposite said first sensor array, to measure an intensity distribution of photons emitted from said scintillation crystal, said intensity distribution characterized by a width which varies with the depth of interaction; wherein the first sensor array provides a measurement of the x- and y-positions of the interaction site and the second sensor array provides a measurement of the depth of interaction.

2. The system as defined in claim 1 further including an entrance window optically coupled to said scintillation crystal and to said second sensor array.

3. The system as defined in claim 1 further including an exit window optically coupled to said scintillation crystal and said first sensor array.

4. The system as defined in claim 1 wherein said second sensor array comprises a wavelength-shifting fiber array.

5. The system as defined in claim 4 wherein said wavelength-shifting fiber array comprises a material which undergoes photo-scintillation upon interaction with the gamma radiation.

6. The system as defined in claim 1 further including computer means for analyzing the intensity distribution of photons sensed by said second sensor array to determine the depth of interaction.

7. The system as defined in claim 1 further including a coincidence imaging radiation source selected from the group consisting of a radioisotope and a positron source.

8. The system as defined in claim 1 wherein said second sensor array is selected from the group consisting of photoscintillation crystals, charge coupled devices and a plurality of spiral shaped collectors.

9. The system as defined in claim 1 further including a reflector layer disposed adjacent said second sensor array.

10. The system as defined in claim 4 wherein the wavelength-shifting fibers are grouped in bundles and adjacent bundles are coupled to different sensors within said first sensor array.

11. A method of determining an interaction site of a gamma ray in a scintillation crystal, comprising the steps of:
    generating gamma radiation with a gamma radiation source;
    generating a first photon output in a scintillation crystal which has interacted with the gamma radiation at an interaction site within the scintillation crystal, the interaction site characterized by an x-position, a y-position, and a depth of interaction;
    detecting the first photon output using a first sensor array disposed on one side of the scintillation crystal and converting the first photon output into x-position and y-position information;
    generating a second photon output from said scintillation crystal which has interacted with the gamma radiation at the interaction site; and
    detecting the second photon output using a second sensor array disposed on another side of the scintillation crystal, opposite the first sensor array, and analyzing the second photon output to determine the depth of interaction.

12. The method as defined in claim 11 wherein the source of gamma radiation is selected from the group consisting of a positron source and a radioactive isotope.

13. The method as defined in claim 11 wherein the second sensor array is a wavelength-shifting fiber array.

14. The system as defined in claim 1, further comprising an analytical expression capable of predicting the intensity distribution of photons reaching the second sensor array.

15. The system as defined in claim 1, wherein said first sensor array is selected from the group consisting of multianode photomultiplier tubes, avalanche photodiodes, spiral shaped multiplier collectors, charge coupled devices, and photomultiplier tube arrays.

16. The system as defined in claim 1, wherein the first sensor array is an array of green-sensitive photomultiplier tubes.

17. The method as defined in claim 11, wherein the gamma radiation source is located within a patient and the x-position, y-position, and depth of interaction information is used to locate the gamma radiation source in the patient.

18. A method for determining the position of interaction of a gamma ray in a scintillation crystal comprising:

disposing a first sensor array on one side of a scintillation crystal;

disposing a second sensor array on the opposite side of the scintillation crystal;

subjecting the scintillation crystal to gamma radiation that interacts with the crystal at an interaction site characterized by an x-position, a y-position, and a depth of interaction to emit photons; wherein the photons are detected by the first and second sensor array as intensity distributions;

determining the x and y positions of the site of interaction from the intensity distribution at the first sensor array; and determining the depth of interaction from the intensity distribution at the second sensor array.

19. The method as defined in claim 18 wherein the depth of interaction is determined by comparing the width of the intensity distribution received by the second sensor array to a standard set of intensity distributions.

20. The method as defined in claim 19 wherein the standard set of intensity distributions are calculated using an analytical expression capable of predicting the intensity distribution of photons reaching the second sensor array.

21. A nuclear imaging system comprising the system for determining an interaction site of a gamma ray in a scintillation crystal as defined in claim 1.

22. The nuclear imaging system as defined in claim 21, wherein the nuclear imaging system is selected from the group consisting of a single head gamma camera, a dual head gamma camera, and a positron emission tomography system.

23. A system for determining the depth of interaction for a gamma ray in a scintillation crystal comprising:

a scintillation crystal for interacting with gamma radiation to emit photons, the interaction occurring at an interaction site within the scintillation crystal characterized by a depth of interaction;

a sensor array disposed on one side of the crystal, wherein the sensor array is capable of measuring an intensity distribution of photons emitted from the scintillation crystal; and an analytical expression capable of predicting the relationship between the depth of interaction and the intensity distribution.

24. The system as defined in claim 23 wherein the sensor array is an array of wavelength-shifting fibers.

25. The system as defined in claim 23 wherein the analytical expression is derived from an optical model of an interaction between a scintillating crystal and a gamma ray.

* * * * *

UNITED STATES PATENT AND TRADEMARK OFFICE
CERTIFICATE OF CORRECTION

PATENT NO.     : 6,459,085 B1                                    Page 1 of 1
DATED          : October 1, 2002
INVENTOR(S)    : Wei Chang et al.

It is certified that error appears in the above-identified patent and that said Letters Patent is hereby corrected as shown below:

Column 1,
Line 3, please add a Government Interests section to read as -- This invention was made by government support under Contract No. 5 ROI CA51329-05 awarded by the National Cancer Institute. The government has certain rights in this invention. --

Column 10,
Line 48, please delete "backf ace" and replace it with -- backface --.

Column 12,
Line 30, please make "B. Oblique Incidence" a stand alone heading and start the sentence "The coincidence line is oblique ..." on the next line.

Signed and Sealed this

First Day of April, 2003

JAMES E. ROGAN
*Director of the United States Patent and Trademark Office*